(12) United States Patent
Ash

(10) Patent No.: US 11,744,983 B2
(45) Date of Patent: Sep. 5, 2023

(54) CATHETER LOCK SOLUTION COMPRISING SODIUM CITRATE AND BENZYL ALCOHOL

(71) Applicant: HemoCleanse Technologies LLC, Lafayette, IN (US)

(72) Inventor: Stephen R. Ash, Lafayette, IN (US)

(73) Assignee: HemoCleanse Technologies LLC, Lafayette, IN (US)

( * ) Notice: Subject to any disclaimer, the term of this patent is extended or adjusted under 35 U.S.C. 154(b) by 345 days.

(21) Appl. No.: 16/766,326

(22) PCT Filed: Nov. 21, 2018

(86) PCT No.: PCT/US2018/062240
§ 371 (c)(1),
(2) Date: May 22, 2020

(87) PCT Pub. No.: WO2019/104162
PCT Pub. Date: May 31, 2019

(65) Prior Publication Data
US 2020/0368493 A1    Nov. 26, 2020

Related U.S. Application Data

(60) Provisional application No. 62/590,536, filed on Nov. 25, 2017.

(51) Int. Cl.
*A61M 25/00* (2006.01)
*A61L 2/18* (2006.01)
(Continued)

(52) U.S. Cl.
CPC .......... *A61M 25/0017* (2013.01); *A61L 2/18* (2013.01); *A61L 29/16* (2013.01); *A61L 2101/36* (2020.08); *A61M 2025/0019* (2013.01)

(58) Field of Classification Search
CPC ....... A61M 25/0017; A61M 2025/0019; A61L 2/18; A61L 29/16; A61L 2101/03
See application file for complete search history.

(56) References Cited

U.S. PATENT DOCUMENTS 6,958,049 B1 * 10/2005 Ash .................... A61M 25/0017
604/28
7,749,529 B2 * 7/2010 Ash ......................... A61P 31/00
514/533

(Continued)

OTHER PUBLICATIONS

Shenep et al., Efficacy of Intravascular Catheter Lock Solutions Containing Preservatives in the Prevention of Microbial Colonization, J. Hosp Infect., 2011, 12 pages, vol. 79, Memphis, TN.

(Continued)

*Primary Examiner* — Sean M Basquill
(74) *Attorney, Agent, or Firm* — Taft Stettinius & Hollister LLP

(57) ABSTRACT

This disclosure generally relates to catheters, methods of enhancing the patency of an intravascular catheter and compositions, methods, devices and kits relating to the infusion of a catheter lock solution into an indwelling catheter. Disclosed compositions, methods, devices and kits aid in diminishing the effects of microbial infection in catheters and occlusion of the catheters. A representative lock solution includes about 10% sodium citrate and about 1.5% benzyl alcohol. The solution has a density approximating the density of blood for retention of the solution in a catheter during the lock period.

17 Claims, 5 Drawing Sheets

(51) Int. Cl.
  *A61L 29/16* (2006.01)
  *A61L 101/36* (2006.01)

(56) References Cited

U.S. PATENT DOCUMENTS

| | | |
|---|---|---|
| 8,226,971 B2 | 7/2012 | Ash et al. |
| 8,389,583 B2 | 3/2013 | Ash et al. |
| 8,703,828 B2 | 4/2014 | Ash et al. |
| 9,011,897 B2 * | 4/2015 | Ash .................... A61P 7/08 |
| | | 514/544 |
| 9,629,368 B2 | 4/2017 | Ash et al. |
| 2004/0071769 A1 * | 4/2004 | Farng .................. A61K 9/0014 |
| | | 424/450 |
| 2004/0092890 A1 | 5/2004 | Ash |
| 2010/0191219 A1 * | 7/2010 | Gupta .................. A61L 29/14 |
| | | 604/269 |

OTHER PUBLICATIONS

International Search Report, International Searching Authority, International Patent Application No. PCT/US18/62240, dated Jan. 24, 2019, 2 pages.

Written Opinion, International Searching Authority, International Patent Application No. PCT/US18/62240, dated Jan. 24, 2019, 6 pages.

International Preliminary Report on Patentability, International Searching Authority, International Patent Application No. PCT/US18/62240, dated May 26, 2020, 7 pages.

* cited by examiner

Antimicrobial catheter lock solution

| | 50% | 25% | 12.50% | 6.25% | 3.12% | 1.56% | Controls** |
|---|---|---|---|---|---|---|---|
| S.aureus 33591 | - | - | - | - | - | - | +/+ |
| S.aureus 29213 | - | - | - | - | + | + | +/+ |
| MRSA* | - | - | - | - | + | + | +/+ |
| S.epidermidis** | - | - | - | - | - | - | +/+ |
| E.coli 35218 | - | + | + | - | + | + | +/+ |
| E.coli 25922 | - | + | + | + | + | + | +/+ |
| P.aeruginosa 27853 | - | - | + | + | + | + | +/+ |
| E.faecalis* | - | - | - | - | + | + | +/+ |
| P.mirabilis* | - | - | + | + | + | + | +/+ |
| C.albicans 10231 | - | - | - | - | + | + | +/+ |
| C.albicans* | - | - | - | - | - | + | +/+ |

*Hospital isolates
**Neat/Pos controls

% of original concentration of CMBJP

FIG. 5

CATHETER LOCK SOLUTION COMPRISING SODIUM CITRATE AND BENZYL ALCOHOL

CROSS REFERENCE TO RELATED APPLICATION

This Application is a U.S. national phase entry of International App. No. PCT/US18/62240 filed on Nov. 21, 2018 which claims the benefit of U.S. Provisional Patent App. No. 62/590,536 filed Nov. 25, 2017, the contents of which are hereby incorporated by reference herein in their entirety.

FIELD OF THE INVENTION

The present disclosure relates to catheters and methods of enhancing the patency of intravascular catheters. More specifically but not exclusively, this disclosure relates to infusing a 10% sodium citrate with benzyl alcohol lock solution into an indwelling intravascular catheter and to methods of inhibiting infection in an animal having an indwelling intravascular catheter.

BACKGROUND

Approximately 360,000 U.S. patients with end-stage renal disease (ESRD) receive maintenance hemodialysis, approximately 25%—90,000 patients—through catheters. Loss of catheter patency because of thrombosis, an ever-present threat, is a common reason a catheter needs to be replaced, and hemodialysis catheters are routinely locked with an anticoagulant solution between dialysis sessions, in most North America centers, unfractionated heparin. This practice has been associated with an increased risk of hemorrhage and heparin-induced thrombocytopenia. Despite prophylactic use of a heparin-containing lock solution, declining catheter blood flow from intraluminal thrombus underlies the necessity to instill a thrombolytic such as tissue plasminogen activator into the catheter lumens of more than half of hemodialysis catheters in an effort to restore patency.

The greatest threat to the safety of patients dialyzed through catheters is catheter-related bloodstream infection (CRBSI); rates in recent prospective studies have ranged from 2 to 5 cases per 1000 catheter-days. CRBSI also commonly results in loss of the catheter and is associated with significant morbidity, including septic shock and a greatly increased risk of infective endocarditis, and has an attributable mortality of at least 10%. It has been estimated that between 67,500 and 150,000 U.S. dialysis patients acquire a CRBSI each year.

In order for microorganisms to cause CRBSI they must first gain access to the extraluminal or intraluminal surface of the implanted device where they can adhere and become incorporated into a biofilm that allows sustained colonization and, ultimately, hematogenous dissemination. Most CRBSIs originating from permanent cuffed and tunneled central venous catheters are caused by intraluminal contaminants. A promising approach to prevention of these infections involves instilling—locking—an anti-infective solution into each catheter lumen when not in use to prevent colonization of the intraluminal surface by planktonic-phase microorganisms which have gained access and can form a biofilm on the inner wall of the catheter. A wide variety of anti-infective lock solutions have been studied in randomized trials for prevention of CRBSI with hemodialysis catheters, and most have shown benefit.

Measures for prevention of CRBSI are most likely to be effective if they are based on a sound understanding of pathogenesis. With short-term non-cuffed central venous catheters, microorganisms from the patient's skin about the insertion site which gain access extraluminally or intraluminally are the source of most catheter-related BSIs. Over the past decade, U.S. hospitals which have taken a highly organized, systems approach, which starts with formal training of personnel who insert and care for central venous catheters and focuses on limiting femoral vein insertions, use of maximal sterile barriers during catheter insertion, disinfecting insertion sites with tincture of chlorhexidine rather than iodine-based antiseptics, and promptly removing unneeded catheters, have reported striking reductions in the incidence of central venous catheter-associated BSI within their intensive care units.

With long-term intravascular devices, including permanent cuffed and tunneled central venous catheters, most CRBSIs derive from microorganisms that have gained access to the catheter lumen during use of the device. Basic infection control with hemodialysis catheters relies upon the use of maximal sterile barriers at insertion and sterile barriers and chlorhexidine disinfection when accessing the catheter and carrying out insertion site care, and a high level of consistency has been associated with a lower risk of CRBSI. Nonetheless, realizing that the rates of CRBSI reported in recent trials with permanent hemodialysis catheters have ranged between 2 and 5 per 1000 catheter-days, there is clearly a role for innovative technologies designed to prevent microorganisms from colonizing the implanted catheter, negating the impact of poor aseptic technique or unique patient vulnerability.

The antimicrobial catheter lock is an innovative technique of local prophylaxis in which an anti-infective solution is instilled into the catheter lumen and allowed to dwell for a prescribed period of time, in the case of hemodialysis catheters for the 2 to 3 day interval between dialysis sessions. In maintenance hemodialysis, a variety of anti-infective solutions have been evaluated in comparative trials—nearly all of which have been in single centers—including the antibiotics vancomycin, gentamicin, cefotaxime and minocycline, each with heparin; taurolidine in combination with citrate; ethylenediaminetetraacetic acid (EDTA), alone or in combination with antibiotics; citrate, alone or in combination with an antibiotic or taurolidine; and ethanol with heparin. Four recent meta-analyses of the individual prospective randomized controlled trials published since 1997 each found a significant reduction in the overall incidence of CRBSI, with a pooled risk reduction in the range of 0.30 to 0.40. None of the individual trials found any evidence that the use of anti-infective lock solutions promoted antimicrobial resistance. However, eight months after a large outpatient hemodialysis program adopted routine gentamicin-heparin lock prophylaxis for 1488 patients dialyzed in eight units, CRBSIs caused by gram-positive organisms resistant to gentamicin, primarily coagulase-negative staphylococci and enterococci, were encountered; 34 infections were ultimately identified over three years, prompting discontinuation of gentamicin lock prophylaxis. A hemodialysis program in New Zealand recently also reported a modest increase in gentamicin resistance of coagulase-negative staphylococci recovered from CRBSIs after adopting gentamicin locks. It seems clear that anti-infective lock solutions with activity against multi-resistant gram-positive and gram-negative bacteria as well as fungi, but which will not promote antimicrobial resistance, are needed. However, antiseptic compounds such as taurolidine and high concentrations of alcohol kill bacteria by denaturing proteins and carbohydrates. This means that they also denature the clotting factors (which are protein) and tend to increase coagulation within catheters and resultant obstruction. High concentrations of alcohol also tend to weaken or damage the plastic materials used for construction of most central venous catheters.

Prevention of catheter loss from intraluminal thrombosis poses a major challenge to stable vascular access in hemodialysis. Dialysis centers routinely lock both lumens of the catheter with an anticoagulant solution at the conclusion of each dialysis session. Whereas citrate is commonly employed in Europe, heparin is used most widely in U.S. centers, in concentrations ranging from 1,000 to 10,000 units/mL. Even when the volume of lock solution is matched to the volume of the lumen, a substantial amount leaks into the systemic circulation, and prolonged partial thromboplastin times can persist for up to 4 hours after dialysis.

The use of heparin in the hemodialysis catheter lock solution has been linked to a significantly increased risk of bleeding, especially in children. Heparin-induced thrombocytopenia, which in its full-blown Type 2 form is associated with devastating thromboembolic complications, occurs in 0.5 to 4% of patients on maintenance hemodialysis when heparin is used in the lock solution. Moreover, heparin antibodies, which are now detectable in many chronic hemodialysis patients, have been linked to increased cardiovascular mortality. In 2008 heparin manufactured in China was implicated in thousands of cases of illness and hundreds of deaths around the world because of toxic concentrations of oversulfated chondroitin sulfate in the final product. Finally, there is evidence that heparin promotes biofilm formation. It seems clear that antithrombotic strategies other than heparin are needed to preserve the patency of hemodialysis catheters.

Moderate concentrations of citrate in a lock solution, in the range 4 to 10%, have been shown to provide protection against patency failure of permanent hemodialysis catheters comparable to heparin in comparative trials; however, these concentrations have weak antibacterial activity and do not offer protection against infection. Much higher concentrations of citrate, in the range of 10-47%, have antibacterial activity and are further active against bacterial biofilms, and have been shown in randomized clinical trials to reduce the risk of CRBSI. However, these concentrations cause a rapid egress of lock solution from the catheter due to high density of the citrate, and these concentrations of citrate have been linked to fatal cardiac arrhythmias and are unlikely to gain approval from the Food and Drug Administration.

Significant resources are currently being invested in a search for alternative ways to lock catheters and, in particular, to develop formulations that have effective antimicrobial and anticoagulation properties. There is a continuing need for advancements in the field of catheter lock solutions. The present invention addresses this need.

SUMMARY

Disclosed herein are compositions, methods, devices and kits relating to the infusion of a catheter lock solution into an indwelling catheter.

In one aspect of the disclosure, a catheter lock solution is used to prevent clotting of central venous catheters and to kill bacteria contaminating the interior lumen of the catheters comprising about 10% concentration of sodium citrate dihydrate, and 0.5 to 1.5% benzyl alcohol.

In a further aspect of the disclosure, the catheter lock solution is adjusted to a pH range of about 6.0 to about 6.5 by addition of citric acid or other form of acid.

In additional aspects of the disclosure, a method to prevent clotting of central venous catheters and to kill bacteria contaminating the interior lumen of the catheters using a catheter lock solution comprising a 10% concentration of sodium citrate dihydrate, and 0.5 to 1.5% benzyl alcohol.

In one form, the disclosure provides aqueous antimicrobial solution comprising about 9 to about 11% by weight citrate and about 1.0 to about 2.0 percent by weight benzyl alcohol dispersed or dissolved therein. In one embodiment, the aqueous antimicrobial solution is an aqueous catheter lock solution. The citrate and the benzyl alcohol preferably have concentrations effective to eliminate infection and to reduce the likelihood of subsequent infections. The citrate can advantageously be provided in the form of trisodium citrate dihydrate (referred to herein as "citrate") or other citrate salt. The relative density of the solution is selected in certain embodiments to be similar to the relative density of a patient's blood, and to thereby optimize the length of time that the solution remains in a catheter. The solution in other embodiments also includes a viscosifying agent and/or additional pharmaceutically acceptable materials.

In another form, the present disclosure provides a method for treating patients having an indwelling intravascular catheter. In one embodiment, the method comprises selecting a patient having an indwelling catheter defining a lumen therethrough; and infusing an aqueous catheter lock solution into the lumen, the solution comprising citrate and benzyl alcohol dispersed or dissolved therein according to any embodiment described in this disclosure. The disclosure is particularly useful in treating a patient having an infection or a substantial risk of infection related to the presence of the catheter.

In yet another form of the disclosure, there is provided an infusion device for infusing a lock solution into a lumen of a catheter. The device includes a syringe and a pharmaceutically acceptable lock solution contained within the syringe. The lock solution includes citrate and benzyl alcohol dispersed or dissolved therein according to any embodiment described in this disclosure. In a preferred embodiment, the syringe containing the lock solution is sterilized.

The disclosure also provides a method of treating animals having a surgically implanted catheter. The method includes infusing into the catheter a pharmaceutically acceptable lock solution comprising a bactericidal component that consists essentially of citrate and benzyl alcohol according to any embodiment described in this disclosure. In a preferred embodiment, the bactericidal component does not include an antibiotic.

In another form, the present disclosure provides a kit for locking a patient's catheter. The kit includes a container having therein a catheter lock solution comprising citrate and benzyl alcohol dispersed or dissolved therein according to any embodiment described in this disclosure; and instructions, recorded in a medium, for infusing the solution into a lumen of an indwelling catheter.

While the actual nature of the disclosure covered herein can only be determined with reference to the claims appended hereto, certain forms and features, which are characteristic of the preferred embodiments disclosed herein, are described briefly follows.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 5 is a chart summarizing the MIC of C/MB/P versus several pathogens (ATCC and hospital isolates) expressed as % of the original concentration of C/MB/P.

Figure 1:
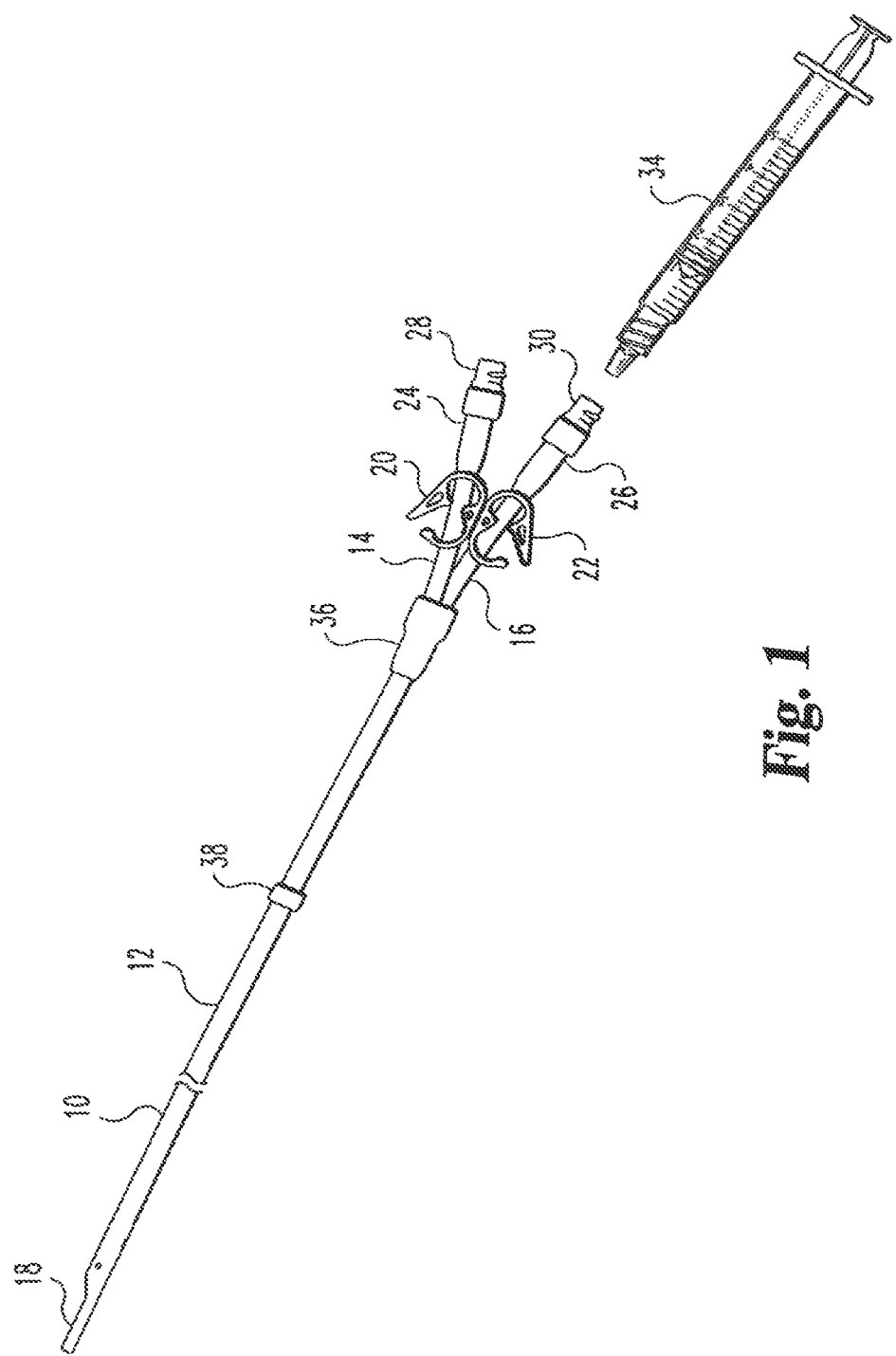
FIG. 1 is a perspective view of one embodiment of a catheter and syringe for infusing a lock solution into a catheter for use with the present disclosure.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION

For the purposes of promoting an understanding of the principles of the invention, reference will now be made to the embodiments disclosed herein and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated herein. Moreover, it should be understood that when certain values and ranges are recited herein in connection with various embodiments of the present teachings, all values and ranges which fall between such listed values and ranges are intended to be encompassed by the present teaching unless explicitly stated otherwise. Finally, although specific methods and materials are described herein with respect to certain exemplary aspects of the present teachings, it should be understood and appreciated that other methods and materials similar or equivalent to those described herein can be used in the practice or testing of the present application without straying from the invention's intended scope.

The embodiments disclosed below are not intended to be exhaustive or limit the disclosure to the precise forms disclosed in the following detailed description. Rather, the embodiments are chosen and described so that others skilled in the art may utilize their teachings.

In one aspect, the present disclosure provides a catheter lock solution operable to provide anticoagulant and antibacterial properties to an implanted catheter as the lock solution resides in the catheter between uses. As used herein, the term "lock solution" refers to a solution that is injected or otherwise infused into a lumen of a catheter with the intention of allowing at least a portion of a lock solution to remain in the lumen until it is desired or required to access that particular lumen again, typically for additional treatment, i.e., infusion or withdrawal of fluid. It is desired that at least a portion of the lock solution remain in the lumen for a desired amount of time lasting from about 1 hour to 3 or 4 days or longer. However, frequently the lock solution is changed on a daily basis during regular care and sterile maintenance of the indwelling catheter. Use of a lock solution in accordance with the present disclosure provides particular advantages for patients with catheters by inhibiting catheter-related infections and by preventing catheter occlusion.

A catheter used in connection with the present disclosure typically can either be an acute (temporary) or chronic (long-term) catheter surgically implanted in an animal. The catheter usually is inserted into a vein or artery, but can be inserted into any other liquid-filled cavity of the body. The catheter is typically used in varying intervals to administer fluids, nutrients, and medications into the body. The catheter also can be used to withdraw body fluids, such as blood for hemodialysis treatment. When not in use, the catheter remains in its position, commonly an intravascular position, until a subsequent treatment is performed.

The catheters that may be used in accordance with this disclosure include known and commonly used catheters and are readily available from a variety of commercial sources. The catheters may vary in configuration and size. One type of catheter commonly used in accordance with this disclosure is a tunneled catheter that includes a cuff for ingrowth of tissue to anchor the catheter. Catheters containing totally subcutaneous ports are also useful in the present disclosure. The catheters are manufactured to function for several months with proper intervention. However, in actual practice prior to the present disclosure, the catheters have exhibited limited longevity because of occlusion and/or infection. The catheters frequently must be removed and/or replaced upon the occurrence of occlusion and/or infection.

FIG. 1 depicts one example of a catheter 10 for use with this disclosure. Catheter 10 is a dual lumen catheter and includes an outer sheath 12 having a cuff 38 and first and second lumens 14 and 16, respectively. Lumens 14 and 16 extend from distal tip 18 through sheath 12 and exit from sheath 12 at connection 36. Each of lumens 14 and 16 include releasable clamps 20 and 22, respectively. Each of lumens 14 and 16 terminate in a threaded end 24 and 26, which can be threadedly attached to protective end caps 28 and 30, respectively. Fluids including a lock solution can be infused or withdrawn from each lumen 14 and 16 by making a Luer connection between a syringe 34 and the ends 24 and 26 of catheter 10. Alternatively, fluids can be infused or withdrawn from each lumen by inserting a needle (not shown) through protective end caps 28 and/or 30 after protective end caps 28 and/or 30 have been sterilized by cleaning successively, for example with Betadine and alcohol. As yet another alternative, one or both protective end caps 28 and 30 can be removed and threaded ends 24 and 26 can be threadedly attached via a connector (not shown) to lines for infusion or withdrawal of fluids (not shown). Once a desired treatment session has been completed, the lumens are typically flushed with normal saline, after which a lock solution is injected into each lumen and fresh, sterile protective end caps are placed on the ends 24 and 26 of the catheter. All procedures are performed using standard sterile techniques well known to these skilled in the art. The catheters for use with this disclosure can be prepared from a variety of materials, including, for example, silicon, polyurethane, polyurethane-polycarbonate copolymer, polyvinyl, silicone, or silastic elastomer.

In one form, the present disclosure provides a catheter lock solution including citrate and benzyl alcohol dispersed or dissolved therein. The citrate in one preferred embodiment is provided in the form of a citrate salt such as, for example, trisodium citrate dihydrate.

In an exemplary citrate/benzyl alcohol catheter lock solution, the total concentration of the benzyl alcohol is from about 0.5 to about 2.0 percent by weight. In another embodiment, the total concentration of the benzyl alcohol is from about 0.5 to about 1.7 percent by weight, and in yet another embodiment, the total concentration of the benzyl alcohol is from about 1.0 to about 1.7 percent by weight.

Although it is not intended that the present disclosure be limited by any theory whereby it achieves its advantageous results, it is believed that the citrate prevents coagulation by chelating the calcium in the adjacent blood. Decreasing the citrate concentration decreases the effect of calcium to catalyze numerous reactions that form blood clots. Citrate as an anticoagulant catheter lock is preferably present at a concentration at least as high as necessary to significantly decrease the ionized calcium concentration in blood, even when the lock solution is diluted by blood at the tip of a catheter. In one preferred embodiment, sodium citrate is present in a lock solution at a concentration of from about 5 to about 11 percent by weight. In another embodiment, citrate is present at a concentration of from about 6 to about 10.5 percent by weight.

The above concentrations are presented as "percent" of mostly trisodium citrate dihydrate in water. When various combinations of salts of citrate are combined, such as trisodium citrate with citric acid, for example to obtain a certain pH, it is more accurate and helpful to express the concentration of citrate as a molar concentration, with a certain percentage of salts being sodium, hydrogen or other cations. Thus, in one embodiment, citrate is present at a concentration of from about 0.17 to about 0.37 Molar. Another embodiment includes citrate at a concentration of from about 0.2 to about 0.36 Molar. Yet another embodiment (9% citrate) includes citrate at a concentration of about 0.31 Molar.

At a citrate concentration of 9% by weight, the citrate has a strong anticoagulant effect in the catheter lock solution. At this concentration, however, it is believed that citrate alone would not provide a significant antimicrobial property. The present disclosure relates to the discovery, which has been experimentally established that a mixture of citrate and benzyl alcohol has unexpected and surprisingly effective antibacterial activity when used as a catheter lock solution in accordance with the present disclosure. In a series of tests with multiple microorganisms, solutions including citrate and benzyl alcohol dispersed or dissolved therein effectively killed all species of bacteria tested (when undiluted), while a solution including heparin and benzyl alcohol has little or no effect on the organisms (allowing growth of a bacterial biofilm).

In one preferred, embodiment, an inventive catheter lock solution includes citrate (provided, for example, in the form of trisodium citrate dihydrate) at a concentration of from about 5 to about 11% by weight and benzyl alcohol having a concentration of from about 0.5 to about 2.0.

In vitro studies have indicated that the density of a lock solution is important in determining the length of time that the lock solution remains in the catheter. The relative density of blood with hematocrit of 32% is approximately 1.050, and increases linearly with hematocrit concentration. If a catheter lock solution with relative density higher than this is placed into a catheter positioned vertically, the lock solution will exit from the catheter at a slow rata. Increasing the viscosity with polymeric substances such as PEG slows but does not prevent the egress of the lock solution. Therefore, in certain embodiments of the disclosure, the citrate concentration in a lock solution is selected such that the density of the lock solution is sufficiently close to the density of the patient's blood that the solution does not exit the catheter during the lock period to an unacceptable degree.

In one aspect of the disclosure, therefore, a catheter lock solution comprising citrate and benzyl alcohol according to any embodiment described in this disclosure is provided that has a density of from about 1.030 to about 1.060 g/ml. In another embodiment, a lock solution comprising citrate and benzyl alcohol has a density of from about 1.035 to about 1.060 g/ml. In still another embodiment, a lock solution comprising citrate and benzyl alcohol is provided having a density of from about 1.040 to about 1.060 g/ml. In yet another embodiment, an inventive lock solution comprising citrate and benzyl alcohol has a density of from about 1.045 to about 1.055 g/ml. It is understood that the density of a given patient's blood may differ from the density of the blood of another patient. Thus, the present disclosure also contemplates matching the relative density of a catheter lock solution to within a predetermined tolerance of the relative density of whole blood of a given patient (such as, for example, within 0.010 g/ml of the relative density of the patient's blood). Such density matching is within the purview of a person of ordinary skill in the art in view of the present description. Closely matching the densities has the advantageous effect of aiding in the retention of the catheter lock solution within the catheter between treatments. When the relative densities are relatively close, gravitational force does not tend to urge the catheter lock solution out of the catheter when the patient is upright. Similarly blood will not enter the catheter when the catheter is upward directed as in the femoral vein when the patient is standing (as can happen with a low-density catheter lock such as heparin).

In another aspect of the disclosure, the catheter lock solution may also include an agent to modify viscosity. The presence of a viscosifying agent is particularly useful, for example, when the relative density of a given catheter lock solution is not the same as the density of a patient's blood.

Therefore, in certain preferred embodiments, a lock solution is provided that comprises citrate and benzyl alcohol according to any embodiment described in this disclosure and one or more agents to adjust viscosity to help retain the lock within the catheter for a desired amount of time. It is well known that catheters are manufactured to have a variety of configurations and lumen diameters. For example, catheters can include single or double lumens. The double lumens can be fused adjacent to each other or they can be concentric. The lumens can have varying cross-sectional areas and shapes, ranging from substantially circular to substantially ovoid. As discussed above, a phenomenon common to most lock solutions is that a portion of the solution at the distal end of the lumen diffuses into the patient's blood stream and is replaced in the catheter by blood. The rate of diffusion of a lock solution from a lumen can be influenced not only by the density of the lock solution, but also by the cross-sectional shape and area of the particular lumen(s) and the viscosity of the lock solution. A lock solution of the present disclosure is preferably prepared to have a viscosity and density such that a substantial portion of the lock solution does not diffuse or flow out of a catheter lumen under normal circumstances within several days.

Viscosifying agents that can advantageously be selected for use in accordance with the present disclosure include those pharmaceutically acceptable agents known or commonly used in treatment of animals including humans. Examples include, but are not limited to, dextran, polyethylene glycol, glycerin, polygeline, and non-metabolizable sugars such as sorbitol and mannitol and mixtures of these compounds. Viscosifying agents that increase the viscosity of a lock solution allow a higher concentration of citrate to be used without having an unacceptable degree of egress of the lock solution from the catheter due to high density of the lock solution.

While it is understood that optimal viscosity and density are dependent upon the shape and size of a particular lumen, a person of ordinary skill in the art, in view of the description herein, can readily determine a desired density and viscosity for a particular catheter without undue experimentation. It is of course understood that the need for viscosifying agents is reduced or eliminated in a lock solution having a relatively low concentration of citrate and a density closely matched to that of blood. The antiseptic effect of the citrate, which is reduced by the reduction in the citrate concentration, is still achieved by the inclusion of benzyl alcohol in an amount whereby the citrate and benzyl alcohol together exhibit an antiseptic effect.

An inventive lock solution according to any embodiment described in this disclosure can be prepared to include a variety of other pharmaceutically acceptable agents. For example, the lock solution can include salts, such as, for example, sodium chloride or other sodium salts. The lock solution can also include a variety of other antibacterial, antimicrobial and anticoagulant agents. Such antibacterial and antimicrobial agents are well known to those skilled in the art and can include, without limitation, gentamicin, vancomycin, and mixtures of these agents. Additional anticoagulant agents that can be included in an inventive catheter lock solution include, for example, heparin, urokinase, tissue plasminogen activation (tPA) and mixtures of these agents. When the anticoagulant includes heparin, the heparin is preferably present at a concentration of from about 100 units/ml to about 10,000 units/ml.

By "pharmaceutically acceptable", it is meant that the lock solution and the included salts and other additives which are, within the scope of sound medical judgment, suitable for use in contact with tissues of humans and lower animals without undue toxicity, irritation, allergic response, and the like, and are commensurate with the reasonable benefit/risk ratio. It is also typically necessary that a composition be sterilized to reduce the risk of infection. For example, pharmaceutically acceptable salts are well-known in the art, and examples can be found in S. M. Berge et al. described in detail in J. Pharmaceutical Science, 66:1-19, 1977.

Compositions described herein can be prepared with simple mixing at room temperature.

In addition to inventive catheter lock solutions, as described above, the present disclosure also provides methods of inhibiting infections in an animal having an indwelling intravascular catheter. In one aspect, therefore, the disclosure provides a method that includes selecting a patient having an indwelling catheter defining a lumen therethrough, and infusing an aqueous catheter lock solution into the lumen, the solution comprising citrate and benzyl alcohol according to any embodiment described in this disclosure dispersed or dissolved therein. In a preferred manner of practicing the disclosure, the method comprises infusing an amount of the lock solution that is from about 80% to about 120% of the internal volume of the catheter being locked.

Once a lock solution is infused into the lumen of a catheter in accordance with the disclosure, it is preferably allowed to remain until it is time to access that particular catheter or lumen again. It is desirable to remove the catheter lock, before starting the dialysis procedure or using the catheter for fluid infusion, especially if the catheter lock solution includes heparin.

In other aspects of the disclosure, the catheter lock solution containing citrate and benzyl alcohol according to any embodiment described in this disclosure may be injected into catheters used for access to other body spaces besides veins or arteries. For example, catheters used in peritoneal dialysis access the peritoneum (the space defined by the peritoneal membrane and exterior to the organs in the abdomen). These catheters also have a risk of bacterial and fungal contamination. After draining and infusing peritoneal dialysate solutions, a lock solution including citrate and benzyl alcohol according to any embodiment described in this disclosure is infused into the catheter. Other catheters with risk of infection include catheters in the urinary bladder, the cerebral spinal fluid (around the central nervous system) and the subcutaneous space (under the skin). The present disclosure contemplates introducing a catheter lock solution as described herein into the lumens of these and other types of catheters.

In another aspect, the disclosure involves an infusion device for infusing a lock solution into a lumen of a catheter. The infusion device includes a syringe and a pharmaceutically acceptable lock solution contained within the syringe, the lock solution including citrate and benzyl alcohol according to any embodiment described in this disclosure dispersed or dissolved therein. In a preferred embodiment, the syringe containing the lock solution is sterilized. The syringe can be advantageously used to infuse a catheter lock solution into a catheter that has an injection port affixed thereto by attaching a needle to the syringe and injecting the needle into the port. Alternatively the syringe can be used by uncapping a catheter and attaching the syringe directly to the catheter.

In another aspect of the disclosure, there is provided a catheter lock kit. In one preferred embodiment, a kit includes a container having therein a catheter lock solution, the catheter lock solution comprising citrate and benzyl alcohol according to any embodiment described in this disclosure dispersed or dissolved therein; and instructions, recorded in a medium, for infusing the solution into a lumen of an indwelling catheter.

Various processes, methods, compositions and devices of the present disclosure are further discussed with reference to the following Examples. It will be understood that these Examples are intended to be illustrative and not restrictive in nature.

EXAMPLES

As an introduction, the present inventor's laboratory was the first to discover that concentrated citrate had antibacterial properties and found that this property is somewhat weak at 7-10% but increases significantly at 23-46%. It also was the first to find that higher concentrations of citrate had problems with egress from catheters, due to a density much higher than that of blood. Subsequent efforts were undertaken to augment the antibacterial function of sodium citrate with various compounds that have been used as preservatives and medications with known antibacterial effects (and which have been administered intravenously without side effects). The objective of this undertaking was to utilize a sodium citrate concentration with density in the range of human blood, but still provide strong antibacterial function. We first found that photo-oxidants such as methylene blue were synergistic with 7% sodium citrate and greatly increased the antibacterial function. We then found that parabens compounds (preservatives) were synergistic with sodium citrate, increasing antibacterial function. Finally, we found that the combination of sodium citrate-parabens-methylene blue (C-MB-P) was even more powerful in killing bacteria, without loss of any of the anticoagulant effects of the citrate.

In clinical trials we demonstrated that C-MB-P offered both an antithrombotic alternative to heparin and protection against CRBSI. In the largest prospective randomized controlled trial to examine the utility of an alternative antithrombotic and an anti-infective lock solution, encompassing 407 patients studied for an aggregate 50,000 catheter-days, we found C-MB-P to be as effective as heparin in preserving catheter patency; none of 201 catheters followed for a mean of 150 days was lost because of patency failure (Maki D G, Ash S R, Winger R K, Lavin P; for the AZEPTIC Trial Investigators. A novel antimicrobial and antithrombotic lock solution for hemodialysis catheters: A multi-center, controlled, randomized trial. Crit Care Med 2011 Vol. 39, No. 4, 613-620.). Moreover, despite a surprisingly low rate of CRBSI in the control group, a tribute to the quality of infection control practice in the study centers, patients in the C-MB-P group had a 71% reduction in CRBSI with protection against all major groups of bacterial pathogens. The solution was at least as safe as heparin, and in the trial showed a strong trend toward reduced all-cause mortality. Comparisons of composite outcome measures combining CRBSI, catheter patency and adverse outcome events, including death from any cause, also showed superiority of the C-MB-P lock solution.

With the results of this large clinical trial, an application for approval to market C-MB-P (by then called Zuragen™) as a catheter lock solution was submitted to the FDA. While working with FDA on the clinical trial protocol and PMA application, catheter lock solutions had been first considered as devices, then combination device-drugs, reviewed both by CDRH (devices) and CDER (drugs). The drug division decided that because methylene blue was considered a drug, Zuragen would be considered a drug. This meant that a second clinical trial would be needed. We also found that methylene blue tended to stain production equipment, meaning production was more expensive than desired. Also, methylene blue when given in large amounts intravenously may cause adverse reactions in some patients taking SSRI medications. Although the amounts of the catheter lock solution used to lock a catheter are too small to cause problems in any patient, drug interaction programs often alert pharmacists of potential adverse reactions between Zuragen and SSRI medications. Also, parabens have been known to cause adverse hormonal effects in some patients if contacted or infused in large quantities. This was another mild marketing hurdle for Zuragen.

In a new study, we created solutions of 10% sodium citrate dihydrate also known as trisodium citrate or sodium citrate, in which the pH was adjusted to 6.2 by addition of 0.4% citric acid. We then added 1.5% benzyl alcohol to this solution. We found that the mixture (C-BA) went into solution somewhat slowly, over 1-2 hours at room temperature, but that the resulting solution was perfectly clear and stable for months at room temperature or at refrigerator temperatures. The density of the final solution was 1.058 g/mL, which is close to the average density of human blood with normal hematocrit (1.050-1.060 g/mL). This means that gravitational forces should not cause the lock solution to exit central venous catheters regardless of the patient's position.

The antibacterial function of C-BA was tested and compared to that of sodium citrate solution without benzyl alcohol (C). To assure that the lock solutions were sterile, we filtered samples after production through 0.2 micrometer membranes. In the following description of procedure, method and results, lock solution identity is as follows:

Lock solution A=10% sodium citrate (C, above)

Lock solution B=10% sodium citrate with 1.5% benzyl alcohol (C-BA, above).

Procedure: "Lock Solution" (LS) A and B were prepared and, before conducting Minimal Inhibitory Concentration (MIC) tests of the solutions, both of them were inoculated into Brain Heart Infusion (BHI) broth and proved to be sterile. Six bacterial strains were recovered from frozen stocks in a −80° C. freezer for each test. Fresh bacteria cultures were incubated with different dilution of each LS in Mueller-Hinton broth (MHB) in 96-well microtiter plates at 37° C. for overnight. Each strain was inoculated in triplicated wells and every experiment was repeated for at least twice. The overall results were calculated, analyzed and interpreted.

Materials and Methods

Chemicals: LS A and B were prepared, stored at 4° C. and used for the experiments at room temperature.

Bacterial strains, growth conditions, sterility test, and pH measurements: Six bacterial pathogens including three Gram-negative bacteria (*Klebsiella pneumoniae* ATCC 33495, *Escherichia coli* O157:H7 EDL 933, and *Pseudomonas aeruginosa* ATCC 10145) and three Gram-positive bacteria (*Staphylococcus aureus* ATCC25923, methicillin-resistant *Staphylococcus aureus* ATCC43300, and *Streptococcus mutans* ATCC25175) were used in this study. All bacterial cultures were procured from American Type Culture Collection (ATCC), Manassas, Va. Bacterial cultures were stored as frozen glycerol (20%) stock at −80° C. A loop of frozen bacterial stock was first streaked on Brain-heart infusion (BHI) agar media and incubated for 18 h at 37° C. to obtain a pure colony. Pure single colony was grown in tryptic soy broth (TSB) for 18 h at 37° C. and 130 rpm. To enumerate bacterial cell density, 18 h grown cultures were serially 10-fold diluted in phosphate-buffered saline (PBS, pH 7.4) and plated on BHI agar plates. Sterility of these catheter lock solutions were also tested by inoculating 100 μL into 4 mL BHI broth and incubated at 37° C.

Minimum Inhibitory Concentration (MIC): The MIC values of LS A and B for six bacterial strains used in this study was determined using micro-titer plate dilution method (Andrews, 2001) after taking spectrophotometric absorbance measurements at 595 nm with micro-titer plate reader (Epoch, BioTek, Winooski, Vt.). All MIC experiments were performed in MHB. 100 μl different dilutions of LS (½, ¼, ⅛, 1/16, 1/32) were mixed with 100 uL of approximately 106 cells bacteria in 2×MHB. Each test was done in triplicate wells of a 96-well microtiter plate, which was further incubated at 37° C. and 70 rpm for 24 h. MHB alone and MHB with bacterial inoculum was used as negative and positive control, respectively. Two experimental replicates were performed to calculate the average MIC value±SD.

Results

Sterility of LS A and LS B samples: After incubating at 37° C. for over 24 hr, there was no turbidity in the BHI broth inoculated with LS A and LS B, suggesting they are sterile.

Minimum inhibitory concentrations (MIC): Inhibition assay performed with LS A (FIG. 2) and LS B (FIG. 3) against the six bacterial pathogens revealed that ½ dilution of LS B inhibits the growth of all pathogens tested. Moreover, the highest concentration of LS A did not significantly suppress the growth of *E. coli* EDL933, *P. aeruginosa* ATCC10145 and *K. pneumoniae* ATCC33459.

Figure 2:
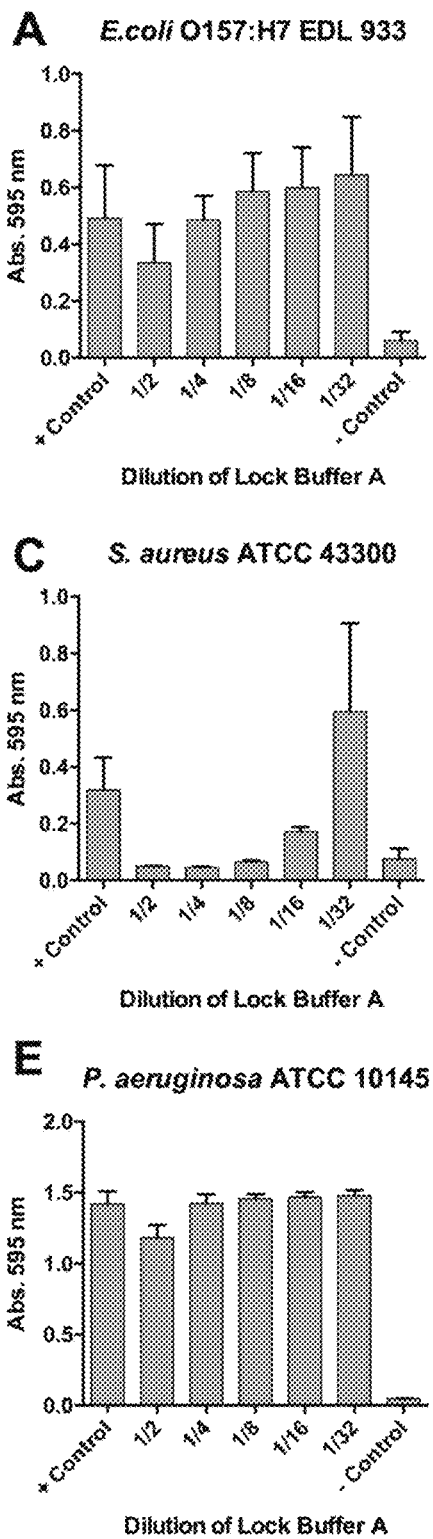
FIG. 2 is a MIC of LS A (Lock Buffer A, sodium citrate) against six pathogens (A) *Escherichia coli* O157:H7 EDL933, (B) *Staphylococcus aureus* ATCC25923 (non-MRSA), (C) *Staphylococcus aureus* ATCC43300 (MRSA), (D) *Streptococcus mutans* ATCC 25175, (E) *Pseudomonas aeruginosa* ATCC10145, (F) *Klebsiella pneumoniae* ATCC33495. + Control, bacterial cultures without treatment, and − Control is media only.
Figure 2:
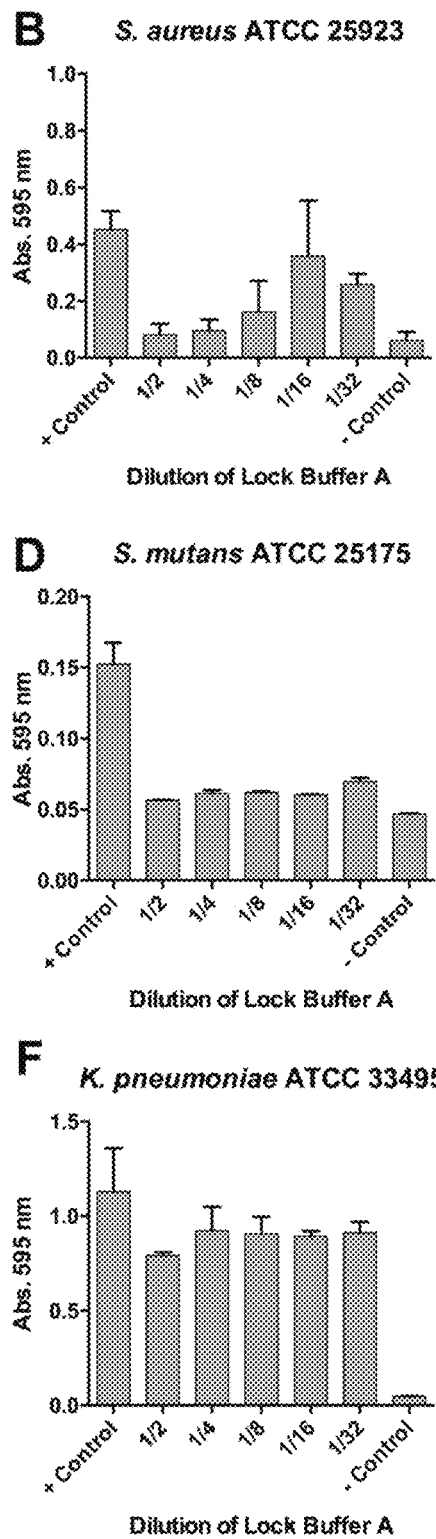
Figure 2:
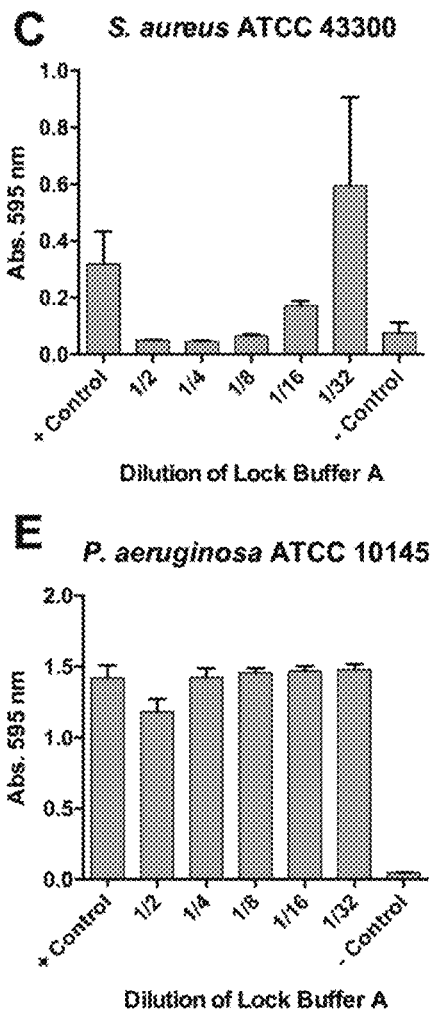
Figure 2:
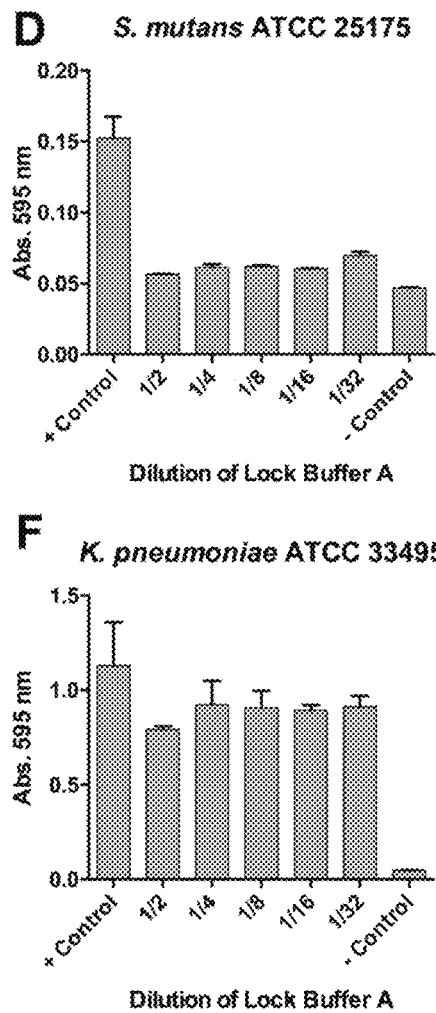
Figure 2:
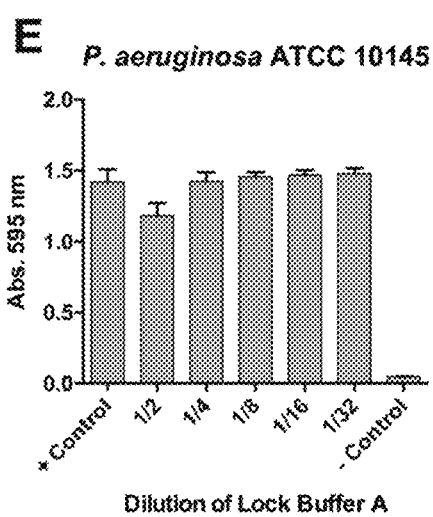
Figure 2:
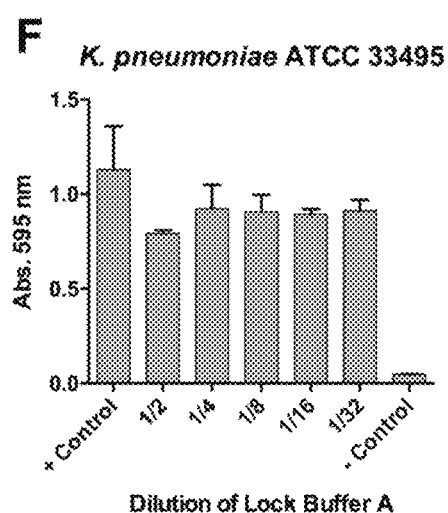
Figure 3:
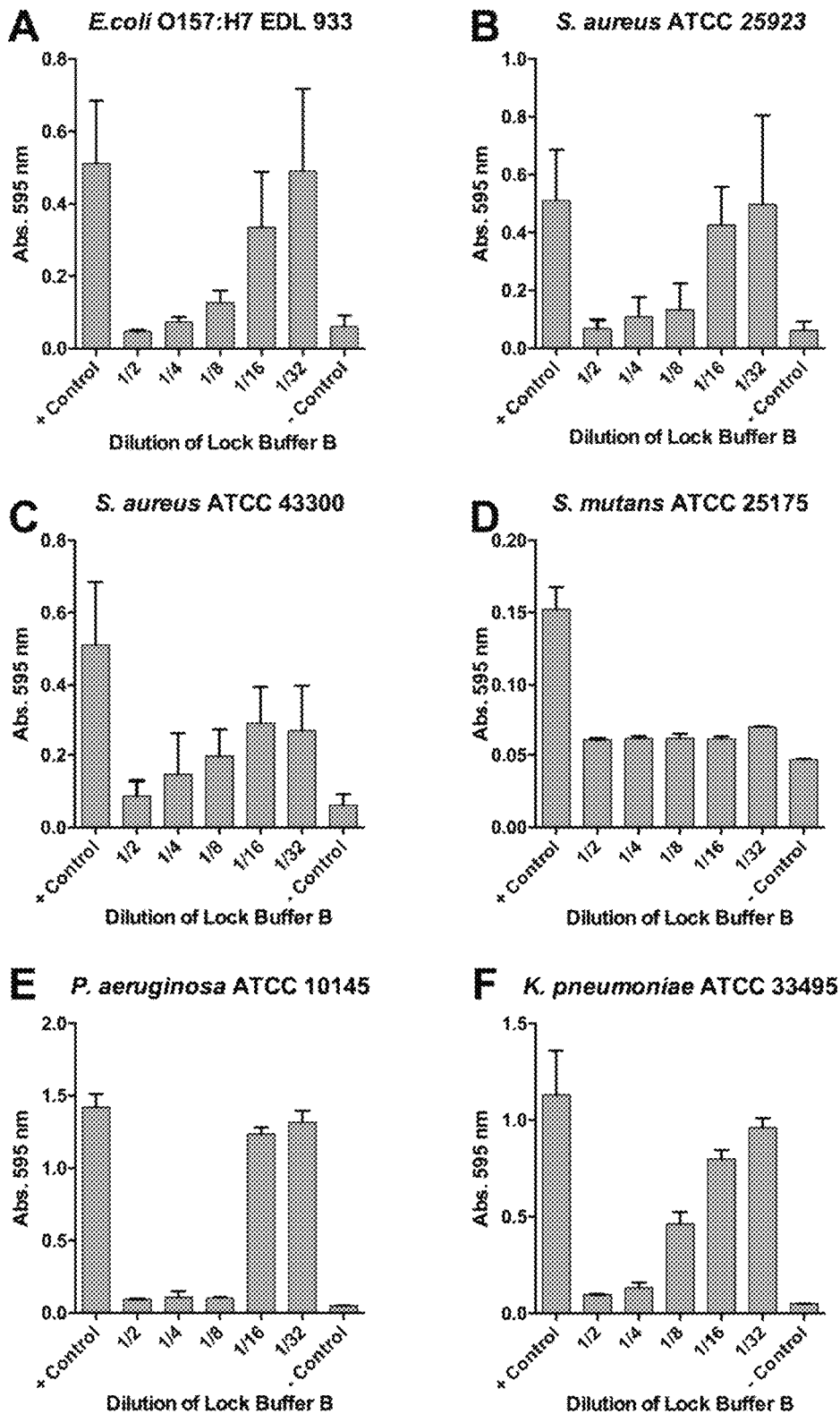
FIG. 3 is a MIC of LS B (Lock Buffer B, sodium citrate with benzyl alcohol) against six pathogens (A) *Escherichia coli* O157:H7 EDL933, (B) *Staphylococcus aureus* ATCC25923 (non-MRSA), (C) *Staphylococcus aureus* ATCC43300 (MRSA), (D) *Streptococcus mutans* ATCC 25175, (E) *Pseudomonas aeruginosa* ATCC10145, (F) *Klebsiella pneumoniae* ATCC33495. + Control, bacterial cultures without treatment, and − Control is media only.

The combination of sodium citrate solution and benzyl alcohol (C-BA) has considerable antibacterial potency. At 1:2 dilution, C-BA completely eliminates growth of all six strains of bacteria tested. This means of course that at full strength it would also eliminate bacterial growth. In fact for gram negative organisms (*E Coli, Pseudomonas* and *Klebsiella*), dilutions of C-BA at 1:8 completely eliminated growth, as shown in FIG. 3. By contrast the sodium citrate solution alone (C) at 1:2 completely eliminated only 3 of the 6 strains of bacteria tested, and none of the gram negative organisms, as shown in FIG. 2. In view of this, together with the testing of benzyl alcohol alone as discussed below, we find that the marked antibacterial effect of C-BA is due to a synergistic antibacterial effect of sodium citrate with benzyl alcohol.

Benzyl alcohol, in the presence of high concentrations of bacteria, would be expected to decrease the bacterial concentration by 2-3 logs (100 to 1000 fold decrease). Benzyl alcohol is commonly added to heparin lock solutions as a preservative. In a previous study, our laboratory tested the antibacterial effect of heparin-benzyl alcohol and found results shown in FIG. 3.

In FIG. 3, the second set of bars shows the reduction of bacteria concentration in biofilm and in planktonic suspensions, in presence of 5000 units/mL heparin with 1% benzyl alcohol. The heparin-benzyl alcohol solution in full strength resulted in a 1-2 log reduction in bacterial number in a suspension of *S. Aureus*. Thus the full-strength concentration of benzyl alcohol alone did not reach inhibitory concentration for bacteria in a heparin solution. This is further evidence that the marked antibacterial effect of C-BA is due to a synergistic antibacterial effect of sodium citrate with benzyl alcohol.

Figure 4:
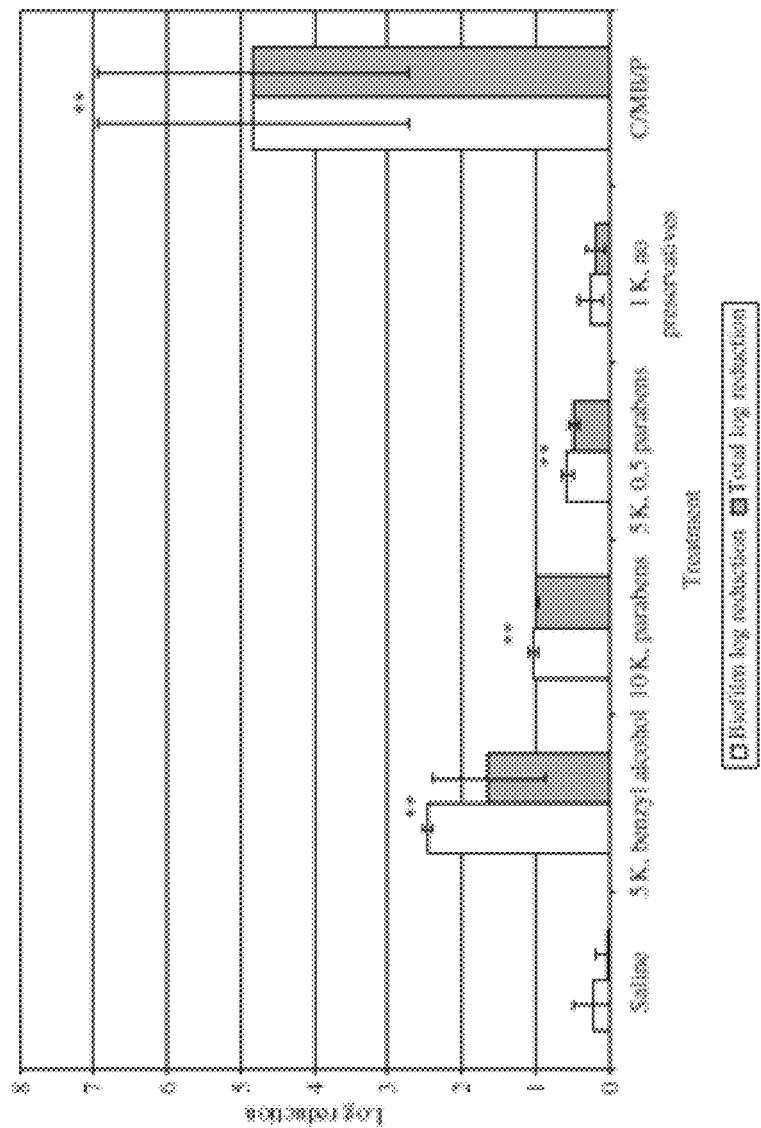
FIG. 4 is a graph of the susceptibility of *S. aureus* biofilms to various tested solutions (heparins, C/MB/P) following 48 h treatment under static conditions. Log reduction for flow cell-grown biofilms (white bars) and for flow cell-grown biofilms plus *S. aureus* cells present in the bulk liquid (grey bars) was determined by viability counts. **$P<0.01$. Error bars indicate 1 SD.

Synergistic effects of sodium citrate with other preservatives such as parabens and with photo-oxidants has been shown by previous work in our laboratory. Our C/MB/P (Zuragen) lock solution combined sodium citrate with methylene blue and parabens. As shown in the FIG. 3, C/MB/P did reach an inhibitory concentration at full strength, in a suspension of *S. aureus*. Further tests demonstrated very high MIC values for all gram positive organisms, but not very high MIC values for gram negative organisms, as shown in FIG. 4.

Gram positive bacteria are the infecting organisms in the majority of catheter related blood stream infections (CRBSI), but almost as many infections are caused by gram negative organisms. It is ideal to have a catheter lock solution that will kill both gram negative and gram positive organisms. C-BA provides more broad-spectrum bacterial killing than C/MB/P, though the MIC level of C/MB/P for gram positives is considerably higher than that for C-BA.

In other studies, we have demonstrated that preservative compounds including alcohols do not adversely affect the antithrombotic effects of sodium citrate. With a sodium citrate concentration of 10% in C-BA, the antithrombotic effects should be considerably more effective than the currently used heparin solutions.

While exemplary embodiments incorporating the principles of the present application have been disclosed herein, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

As will be appreciated by a person of ordinary skill in the art upon reading the information disclosed above, in one aspect, the present disclosure provides an aqueous antimicrobial solution comprising about 5 to about 11% by weight citrate and about 0.5 to about 2.0 percent by weight benzyl alcohol dispersed or dissolved therein. In one embodiment, the concentration of citrate in the solution is at least as high as the calcium concentration in a patient's blood. In another embodiment, the concentration of citrate in the solution is from about 6 to about 10.5% by weight. Additional embodiments include any other embodiment disclosed herein wherein the citrate is trisodium citrate dehydrate. The present disclosure also contemplates all embodiments described herein wherein the pH of the solution is from about 5 to about 7.5. The present disclosure also contemplates all embodiments described herein wherein the pH of the solution is from about 6 to about 7. The present disclosure also contemplates all embodiments described herein wherein the relative density of the solution is from about 1.030 to about 1.060 g/ml. The present disclosure also provides embodiments in which any of the embodiments disclosed above further includes a viscosifying agent. The present disclosure also contemplates all embodiments described herein wherein the viscosifying agent comprises dextran, polyethylene glycol, glycerin, polygeline, a non-metabolizable sugar, or a combination thereof. The present disclosure also contemplates all embodiments described herein wherein the citrate has a concentration of from about 6 to about 10.5% by weight and the concentration of benzyl alcohol is from about 0.5 to about 1.7% by weight.

In another aspect, the present disclosure provides a method of inhibiting infection in an indwelling catheter defining at least one lumen therethrough, the method comprising infusing an aqueous catheter lock solution into a lumen of the catheter, the solution comprising about 5 to about 11% by weight citrate and about 0.5 to about 2.0 percent by weight benzyl alcohol. In one embodiment, the concentration of citrate in the solution is at least as high as the calcium concentration in a patient's blood. In another embodiment, the concentration of citrate in the solution is from about 6 to about 10.5% by weight. Additional embodiments include any other embodiment disclosed herein wherein the citrate is trisodium citrate dihydrate. The present disclosure also contemplates all embodiments described herein wherein the pH of the solution is from about 5 to about 7.5. The present disclosure also contemplates all embodiments described herein wherein the pH of the solution is from about 6 to about 7. The present disclosure also contemplates all embodiments described herein wherein the relative density of the solution is from about 1.030 to about 1.060 g/ml. The present disclosure also provides embodiments in which any of the embodiments disclosed above further includes a viscosifying agent. The present disclosure also contemplates all embodiments described herein wherein the viscosifying agent comprises dextran, polyethylene glycol, glycerin, polygeline, a non-metabolizable sugar, or a combination thereof. The present disclosure also contemplates all embodiments described herein wherein the citrate has a concentration of from about 6 to about 10.5% by weight and the concentration of benzyl alcohol is from about 0.5 to about 1.7% by weight.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method actions, processes, and operations described herein are not to be construed as necessarily requiring their performance in the particular order discussed or illustrated, unless specifically identified as an order of performance. It is also to be understood that additional or alternative actions or operations may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed herein could be termed a second element, component, region, layer or section without departing from the teachings of the example embodiments.

While the invention has been illustrated and described in detail in the drawings and foregoing description, the same is to be considered as illustrative and not restrictive in character, it being understood that only certain exemplary embodiments have been shown and described and that all changes and modifications that come within the spirit of the inventions are desired to be protected.

What is claimed is:

1. An aqueous antimicrobial solution comprising about a synergistic combination of about 7% by weight citrate and about 1.5% by weight benzyl alcohol dispersed or dissolved therein.

2. The solution of claim 1, wherein the citrate is trisodium citrate dihydrate.

3. The solution of claim 1, wherein the pH of the solution is from about 5 to about 7.5.

4. The solution of claim 1, wherein the relative density of the solution is from about 1.030 to about 1.060 g/ml.

5. The solution of claim 1, wherein the solution further comprises a viscosifying agent.

6. A catheter lock solution to prevent clotting of central venous catheters and to kill bacteria contaminating the interior lumen of the catheters comprising:

the aqueous antimicrobial solution of claim 1.

7. The solution of claim 6, in which the pH is adjusted to a range of about 6.0 to about 6.5 by addition of citric acid or other form of acid.

8. A method to prevent clotting of central venous catheters and to kill bacteria contaminating the interior lumen of the catheters using the catheter lock solution of claim 6.

9. A method of inhibiting infection in an indwelling catheter defining at least one lumen therethrough, the method comprising infusing an aqueous catheter lock solution into a lumen of the catheter, the solution comprising a catheter lock solution of claim 6.

10. The method of claim 9 wherein the catheter is an intravascular catheter or a body cavity catheter.

11. The method of claim 9 wherein the lumen of the catheter has an internal volume and the method comprises infusing an amount of the lock solution that is from about 80% to about 120% of the internal volume of the lumen.

12. The method according to claim 9 wherein the citrate is trisodium citrate dihydrate.

13. The method of according to claim 9 wherein the pH of the solution is from about 5 to about 7.5.

14. The method according to claim 9 wherein the relative density of the solution is from about 1.030 to about 1.060 g/ml.

15. The method according to claim 9 wherein the solution further comprises a viscosifying agent.

16. The method according to claim 9, wherein the catheter is in a patient.

17. The method according to claim 16, wherein the catheter is surgically implanted.

* * * * *